(12) United States Patent
Medvedovsky et al.

(10) Patent No.: US 11,844,602 B2
(45) Date of Patent: Dec. 19, 2023

(54) IMPEDANCE-ENRICHED ELECTROPHYSIOLOGICAL MEASUREMENTS

(71) Applicants: The Medical Research Infrastructure and Health Services Fund of the Tel Aviv Medical Center, Tel Aviv (IL); Ramot at Tel Aviv University Ltd., Tel Aviv (IL)

(72) Inventors: Mordekhay Medvedovsky, Beer-Sheva (IL); Tomer Gazit, Tel Aviv (IL); Talma Hendler, Tel Aviv (IL); Evgeny Tsizin-Goldman, Ramat Gan (IL); Alex Bronstein, Haifa (IL)

(73) Assignees: The Medical Research Infrastructure and Health Services Fund of the Tel Aviv Medical Center, Tel Aviv (IL); Ramot at Tel Aviv University Ltd., Tel Aviv (IL)

( * ) Notice: Subject to any disclaimer, the term of this patent is extended or adjusted under 35 U.S.C. 154(b) by 1325 days.

(21) Appl. No.: 16/290,988

(22) Filed: Mar. 4, 2019

(65) Prior Publication Data
US 2019/0269348 A1 Sep. 5, 2019

Related U.S. Application Data

(60) Provisional application No. 62/638,322, filed on Mar. 5, 2018.

(51) Int. Cl.
*A61B 5/00* (2006.01)
*A61B 5/06* (2006.01)
(Continued)

(52) U.S. Cl.
CPC ............ *A61B 5/063* (2013.01); *A61B 5/0033* (2013.01); *A61B 5/0042* (2013.01);
(Continued)

(58) Field of Classification Search
CPC ..... A61B 5/063; A61B 5/0033; A61B 5/0042; A61B 5/0536; A61B 5/30; A61B 5/304;
(Continued)

(56) References Cited

U.S. PATENT DOCUMENTS 3,880,146 A * 4/1975 Everett ............... A61B 5/0006
600/523
4,495,950 A 1/1985 Schneider
(Continued)

FOREIGN PATENT DOCUMENTS

CN 203815454 U 9/2014
CN 104302351 A 1/2015
(Continued)

OTHER PUBLICATIONS

Holder et al.,"Part 1 of Electrical Impedance Tomography: Methods, History and Applications", Institute of Physics Publishing, pp. 1-61, Dec. 21, 2004.
(Continued)

*Primary Examiner* — May A Abouelela
(74) *Attorney, Agent, or Firm* — Kligler & Associates Patent Attorneys Ltd.

(57) ABSTRACT

A diagnostic system includes an array of electrodes, which are coupled to a body surface of a living subject at different, respective positions in proximity to a region of interest within the body. A switched impedance network applies varying loads to the electrodes. A processor is coupled to receive and measure electrical signals from the electrodes as a function of the varying loads, and to analyze the measured signals so as to compute a local electrical characteristic of one or more locations within the region of interest.

28 Claims, 4 Drawing Sheets

(51) Int. Cl.
*A61B 5/0536* (2021.01)
*A61B 5/377* (2021.01)
*A61B 5/30* (2021.01)
*A61B 5/304* (2021.01)
*A61B 5/31* (2021.01)
*A61B 5/383* (2021.01)

(52) U.S. Cl.
CPC .............. *A61B 5/0536* (2013.01); *A61B 5/30* (2021.01); *A61B 5/304* (2021.01); *A61B 5/31* (2021.01); *A61B 5/377* (2021.01); *A61B 5/4064* (2013.01); *A61B 5/6814* (2013.01); *A61B 5/6847* (2013.01); *A61B 5/7235* (2013.01); *A61B 5/383* (2021.01)

(58) Field of Classification Search
CPC ......... A61B 5/31; A61B 5/377; A61B 5/4064; A61B 5/6814; A61B 5/6847; A61B 5/7235; A61B 5/383
See application file for complete search history.

(56) References Cited

U.S. PATENT DOCUMENTS

| | | | |
|---|---|---|---|
| 5,905,489 A | 5/1999 | Takahama et al. | |
| 7,089,059 B1* | 8/2006 | Pless | A61B 5/6864 607/45 |
| 7,130,694 B1 | 10/2006 | Voelkel | |
| 7,697,979 B2 | 4/2010 | Martinerie et al. | |
| 7,809,434 B2 | 10/2010 | Kofol et al. | |
| 8,032,209 B2 | 10/2011 | He et al. | |
| 9,415,214 B2 | 8/2016 | Moore | |
| 10,228,242 B2 | 3/2019 | Abovitz et al. | |
| 2003/0069514 A1 | 4/2003 | Brody | |
| 2004/0006279 A1 | 1/2004 | Arad (Abboud) | |
| 2006/0041203 A1 | 2/2006 | Wolf et al. | |
| 2006/0085049 A1 | 4/2006 | Cory et al. | |
| 2006/0165811 A1 | 7/2006 | Black et al. | |
| 2008/0082012 A1 | 4/2008 | Gunderson et al. | |
| 2008/0132800 A1 | 6/2008 | Hettrick et al. | |
| 2008/0154350 A1* | 6/2008 | Julian | A61N 1/3918 607/119 |
| 2008/0161714 A1 | 7/2008 | Ahonen et al. | |
| 2008/0208284 A1 | 8/2008 | Rezai et al. | |
| 2008/0312523 A1 | 12/2008 | Dunseath | |
| 2009/0033333 A1 | 2/2009 | Gribova et al. | |
| 2009/0054800 A1 | 2/2009 | Martinerie et al. | |
| 2009/0082691 A1 | 3/2009 | Denison et al. | |
| 2011/0257506 A1 | 10/2011 | Baillet et al. | |
| 2011/0319777 A1 | 12/2011 | Mehrotra et al. | |
| 2012/0027058 A1* | 2/2012 | Lynch | A61B 5/0536 375/219 |
| 2012/0101545 A1 | 4/2012 | Wahlstrand et al. | |
| 2012/0157868 A1 | 6/2012 | Pekonen | |
| 2012/0232376 A1 | 9/2012 | Crevecoeur et al. | |
| 2012/0265261 A1 | 10/2012 | Bikson et al. | |
| 2012/0310105 A1 | 12/2012 | Feingold et al. | |
| 2013/0041235 A1 | 2/2013 | Rogers et al. | |
| 2013/0150697 A1 | 6/2013 | Imai et al. | |
| 2013/0217993 A1* | 8/2013 | Brunner | A61B 5/0536 600/393 |
| 2013/0321009 A1 | 12/2013 | Aliakseyeu | |
| 2014/0031952 A1 | 1/2014 | Harshbarger et al. | |
| 2014/0058528 A1 | 2/2014 | Contreras-Vidal et al. | |
| 2014/0198035 A1 | 7/2014 | Bailey et al. | |
| 2014/0257129 A1 | 9/2014 | Choi et al. | |
| 2014/0296941 A1 | 10/2014 | King et al. | |
| 2015/0011857 A1 | 1/2015 | Henson et al. | |
| 2015/0072326 A1 | 3/2015 | Mauri et al. | |
| 2015/0148641 A1 | 5/2015 | Morun et al. | |
| 2015/0157240 A1* | 6/2015 | Shoudy | A61B 5/0536 600/547 |
| 2015/0185853 A1 | 7/2015 | Clausen et al. | |
| 2015/0245928 A1 | 9/2015 | Kao et al. | |
| 2015/0272483 A1 | 10/2015 | Etemad et al. | |
| 2015/0272501 A1 | 10/2015 | Maceachern et al. | |
| 2015/0282768 A1 | 10/2015 | Luna et al. | |
| 2015/0297145 A1 | 10/2015 | Luna et al. | |
| 2015/0359491 A1 | 12/2015 | Luna et al. | |
| 2016/0100803 A1 | 4/2016 | Korzinov et al. | |
| 2016/0354604 A1 | 12/2016 | Kent | |
| 2017/0105648 A1* | 4/2017 | Boverman | A61B 5/6843 |
| 2017/0123528 A1 | 5/2017 | Hu et al. | |
| 2017/0172451 A1* | 6/2017 | Boverman | G06T 11/003 |
| 2017/0238812 A1 | 8/2017 | Atlas | |
| 2018/0028810 A1 | 2/2018 | Schwarz et al. | |
| 2018/0036531 A1 | 2/2018 | Schwarz et al. | |
| 2018/0153432 A1* | 6/2018 | Skrabal | A61B 5/304 |
| 2018/0279939 A1 | 10/2018 | Madsen et al. | |
| 2019/0328277 A1* | 10/2019 | Woo | A61B 5/6822 |
| 2019/0336035 A1* | 11/2019 | Dichterman | A61B 5/6852 |
| 2019/0357796 A1* | 11/2019 | Tanaka | H02J 7/0042 |
| 2019/0365280 A1* | 12/2019 | Shmayahu | A61B 5/7253 |
| 2019/0387997 A1* | 12/2019 | Franck | A61B 5/282 |
| 2020/0060547 A1* | 2/2020 | Hill | A61B 5/0035 |
| 2020/0282223 A1 | 9/2020 | Schwemmer et al. | |

FOREIGN PATENT DOCUMENTS

| | | |
|---|---|---|
| CN | 105266807 A | 1/2016 |
| WO | 2010129026 A1 | 11/2010 |
| WO | 2014051590 A1 | 4/2014 |
| WO | 2014208074 A1 | 12/2014 |
| WO | 2015100482 A1 | 7/2015 |

OTHER PUBLICATIONS

Kemppainen et al., "Channel capacity of multichannel magnetometers," Advances in Biomagnetism, Plenum Press, pp. 635-638, year 1989.
Elazar et al., "Impedance Changes during Epileptic Seizures", Epilepsia Journal, Elsevier Publishing Company, vol. 7, issue 4, pp. 291-307, year 1966.
Nenonen et al., "Total information of multichannel MEG sensor arrays," Proceedings of the 14th International Conference on Biomagnetism, Boston, USA, pp. 630-631, Aug. 8-12, 2004.
Cuffin et al., "Tests of EEG Locahzation Accuracy Using Implanted Sources in the Human Brain", Annals of Neurology, vol. 29, issue 2, pp. 132-138, Feb. 1991.
CN Application # 201780043260.9 Office Action dated Jan. 24, 2022.
U.S. Appl. No. 16/316,627 Office Action dated Jan. 27, 2022.
U.S. Appl. No. 16/316,627 Office Action dated Aug. 30, 2021.
Tommaso., "Parallel Modeling of the Electric Field Distribution in the Brain", Doctor Thesis, Alma Mater Studiorum—University of Bologna, Cycle XXIII—ING-INF/01, pp. 1-135, year 2011.
Frank., "An Accurate, Clinically Practical System for Spatial Vectorcardiography", Circulation, vol. XIII, May, pp. 737-749, year 1956.
Nenonen et al., "Total information extracted from MEG measurements", International Congress Series 1300, pp. 245-248, year 2007.
International Application # PCT/IB2017/054196 search report dated Oct. 23, 2017.
Hamalainen et al., "Magnetoencephalography—Theory, Instrumentation and Applications to the Noninvasive Study of Human Brain Function", Reviews of Modern Physics, vol. 65, No. 2, pp. 413-497 + 8 sheets of figures, Apr. 1993.
Wolters et al., "A Parallel Algebraic Multigrid Solver for Finite Element Method Based Source Localization in the Human Brain", Computing and Visualization in Science, pp. 165-177, year 2002.
Bronstein et al., U.S. Appl. No. 16/316,627, filed Jan. 10, 2019.

* cited by examiner

IMPEDANCE-ENRICHED ELECTROPHYSIOLOGICAL MEASUREMENTS

CROSS-REFERENCE TO RELATED APPLICATION

This application claims the benefit of U.S. Provisional Patent Application 62/638,322, filed Mar. 5, 2018, which is incorporated herein by reference.

FIELD OF THE INVENTION

The present invention relates generally to signal processing, and particularly to apparatus and methods for acquiring and processing electrophysiological signals.

BACKGROUND

Electroencephalography (EEG) is a technique for noninvasive measurement of the electrical potentials over the scalp, aiming to reconstruct the underlying primal electrical activity of the brain cortex. EEG is a valuable tool both for diagnosis of neurological diseases (epilepsy being a well-known example) and for research.

Despite its clinical importance, conventional EEG measurement is capable of only low spatial and temporal resolution. One reason for the low spatial resolution is the unsolved complexity of electrical conductivity distribution within the head. Another reason is the influence of the skull on the propagation of electrical signals from the neural sources to the scalp: The skull effectively acts as a spatial low-pass filter. The EEG itself is limited in temporal frequency to the range below about 100 Hz. These constraints place a bound on the information that can be extracted from an EEG signal.

Electrical impedance tomography (EIT) is a medical imaging technique that infers and displays the electrical conductivity, permittivity, and/or impedance of a part of the body based on surface electrode measurements. Typically, conducting body-surface electrodes are attached to the skin around the body part being examined. Small alternating currents are applied to some or all of the electrodes, and the resulting voltages sensed by the other electrodes are recorded. This process is repeated for numerous different electrode configurations and finally results in reconstruction of a tomographic image, using image reconstruction algorithms that are known in the art.

SUMMARY

Embodiments of the present invention that are described herein provide improved systems and methods for processing and localizing electrophysiological signals.

There is therefore provided, in accordance with an embodiment of the invention, a diagnostic system, including an array of electrodes, which are configured to be coupled to a body surface of a living subject at different, respective positions in proximity to a region of interest within the body. A switched impedance network is configured to apply varying loads to the electrodes. A processor is coupled to receive and measure electrical signals from the electrodes as a function of the varying loads, and to analyze the measured signals so as to compute a local electrical characteristic of one or more locations within the region of interest.

In the disclosed embodiments, the switched impedance network includes a plurality of impedance components interconnected by analog switches, and the impedance components are selected from a group of components consisting of resistors and capacitors.

In some embodiments, the electrodes are configured to sense an electrical activity in the body having a maximal frequency, and the processor is configured to receive and measure the electrical signals due to the sensed electrical activity while varying the loads applied by the switched impedance network at a rate greater than twice the maximal frequency, and possibly at least ten times the maximal frequency. In a disclosed embodiment, the region of interest is a head of the subject, and wherein the electrodes are configured to sense an electroencephalogram (EEG) of the subject.

In some embodiments, the system includes a field generator, which is configured to generate a time-varying electric field within the region of interest, and the processor is configured to measure the electrical signals output from the electrodes in response to the time-varying electric field. In one embodiment, the field generator includes a driver, which is coupled to drive an electrode coupled to the body of the subject to generate the time-varying electric field. In another embodiment, the field generator is incorporated in an implantable device. The processor may be configured to localize the implantable device within the body by analyzing the measured signals.

In still another embodiment, the processor is configured to analyze the measured signals so as to identify a location of a source of a signal within the region of interest.

In some embodiments, the processor is configured to analyze the measured signals so as to estimate local electrical impedances of one or more locations within the region of interest. In a disclosed embodiment, the processor is configured to estimate the local electrical impedances by find a matrix of the impedances between the electrodes in the array, and associating the matrix of the impedances with the respective positions of the electrodes in order to find the local electrical impedances of the one or more locations. The processor may be configured to generate and output an electrical impedance tomogram incorporating the local electrical impedances.

There is also provided, in accordance with an embodiment of the invention, a diagnostic method, which includes coupling an array of electrodes to a body surface of a living subject at different, respective positions in proximity to a region of interest within the body. Varying loads are applied to the electrodes using a switched impedance network connected to the electrodes. Electrical signals from the electrodes are received and measured as a function of the varying loads. The measured signals are analyzed so as to compute a local electrical characteristic of one or more locations within the region of interest.

The present invention will be more fully understood from the following detailed description of the embodiments thereof, taken together with the drawings in which:

DETAILED DESCRIPTION OF EMBODIMENTS

Overview

The embodiments of the present invention that are described hereinbelow relate primarily to EEG and measurement of local electrical characteristics of tissue within the brain. These embodiments address the difficulty in noninvasively extracting local electrical information, due to the spatial complexity of the brain on the one hand and the low-pass filtering effect of the skull on the other.

In contrast to the low spatial and temporal frequencies of the EEG, current technologies allow sampling of electrical signals at rates up to tens of GHz. There is thus an enormous gap between the technological potential for information acquisition and the actual information extraction from EEG by current methods. This gap cannot be filled via algorithmic solutions alone. Therefore, the present embodiments offer distinct physical solutions, using switched impedance networks. Although these solutions are described below specifically with reference to the brain, the principles of the disclosed embodiments may alternatively be applied, mutatis mutandis, to other organs and regions of interest within the body of a living subject, such as the thorax, and these alternative applications are considered to be within the scope of the present invention.

The EEG forward problem relates the distribution of the electrical potentials M measured by electrodes on the scalp of the subject's head to a given distribution of the primary current sources X (assuming that X is known) and the electrical conductivity within the head. The inverse EEG problem is to find the distribution of current sources from the measurements on the scalp. In the disclosed embodiments, a switched impedance network is used in applying varying loads to the electrodes, thus creating temporal variations in the boundary conditions of the EEG forward problem and, by the same token, adding independent equations to the inverse problem. In some embodiments, the loads are varied at a rate at least twice the maximal frequency of the biological signals that are being measured (for example, 100 Hz in the case of EEG), or even ten times the maximal frequency. Alternatively, since the EEG signals can be averaged over a number of distinct measurement periods, the effective number of equations can be increased even if the impedance network is static within a trial but is altered between different measurement periods.

Thus, in the disclosed embodiments, a diagnostic system, comprises an array of electrodes, which are coupled to the body surface of the subject at different, respective positions in proximity to a region of interest within the body, for example the brain. A switched impedance network applies varying loads to the electrodes. A processor receives and measures electrical signals from the electrodes as a function of the varying loads, and analyze the measured signals so as to compute local electrical characteristics of locations within the region of interest.

The above-mentioned provisional patent application provides a detailed theoretical background for the operation of these embodiments (see particularly pages 6-21 in the provisional specification). These theoretical details will be omitted from the following description for the sake of brevity.

Some embodiments of the present invention can be applied, for instance, in addressing the problem that EEG measurements are often incapable of distinguishing between a strong deep current dipole source within the brain and a weak source close to the surface. Moreover, it may be impossible to distinguish between a deep source within the brain and the electrical signal resulting from muscle activation under the scalp. The disclosed embodiments can be used to discriminate between these activities, since they produce different responses in different parts of the impedance network. In preliminary trials, the inventors were able to remove typical EEG artifacts such as cardiac signals and signals due to blinking, jaw and neck muscle movement.

Additionally or alternatively, the switched impedance network can be applied to increase spatial resolution when electrodes are placed on the scalp with a density above the spatial Nyquist frequency of the EEG signals. This approach can be used in making passive impedance measurements of the brain tissue, in conjunction with or independently of an implanted device. The switched impedance network used in the present embodiments makes it possible to measure impedance passively—meaning that the measurement is made without having to apply electrical signals to the brain—by comparing electrical potentials between electrodes interconnected by shunting impedances that vary in space and/or in time. In this situation, the brain currents themselves can serve as the electrical source for impedance measurement, thus avoiding possible adverse health effects arising from the application of alternating electrical currents to the brain.

The measurement of local electrical impedances in this manner can be used in generating electrical impedance tomograms (EITs), and can also provide information regarding early ictal changes, which are reflected in local impedance variations within the brain. These measurements can be used in conjunction with an implanted device, for example, in closed loop neuro-stimulation in order to suppress development of epileptic seizures.

In some embodiments of the present invention, the electrical signals measured as a function of the varying loads applied by the switched impedance network are processed in order find a matrix of impedances between the electrodes that are applied to the body surface (referred to as the Z-matrix). This matrix is associated with the respective positions of the electrodes in order to map the local electrical impedances to location coordinates within the body, and thus generate the EIT. The theoretical basis for the Z-matrix and derivation of the matrix using varying loads on the electrodes is described in detail in the Appendix of the above-mentioned provisional patent application (particularly pages 1-6), and is omitted here for the sake of brevity.

The electrical signals that are measured for the purposes of EIT in these embodiments may be due to existing fields resulting from biological activity (such as EEG, ECG or EMG), as noted above, or even due to electrical noise from power lines or from the communication signal of a device that is implanted in the subject's body. This passive approach is advantageous, particularly (though not exclusively) when applied in conjunction with implantable and wearable devices. Potential advantages include reduced power consumption, immunity to electrical noise, minimized current injection into biological tissues, diminished nonlinear effects due to current injection, cost effectiveness, and the possibility of monitoring changes in bio-impedance at frequencies overlying the spectrum of electrophysiological signals that are being monitored, such as EEG.

In another embodiment, passive impedance measurement is combined with local drug delivery using catheters, for example. In such cases impedance monitoring can detect tissue reaction to the delivered drug, such as hyperemia, inflammation or gliosis. Such embodiments can be applied, inter alia, in closed-loop electrophoretic drug delivery and in catheter-based drug delivery to brain tumors. In this latter case, passive impedance monitoring can detect changes of tissue impedance associated with bleeding or edema.

System Description

Figure 1:
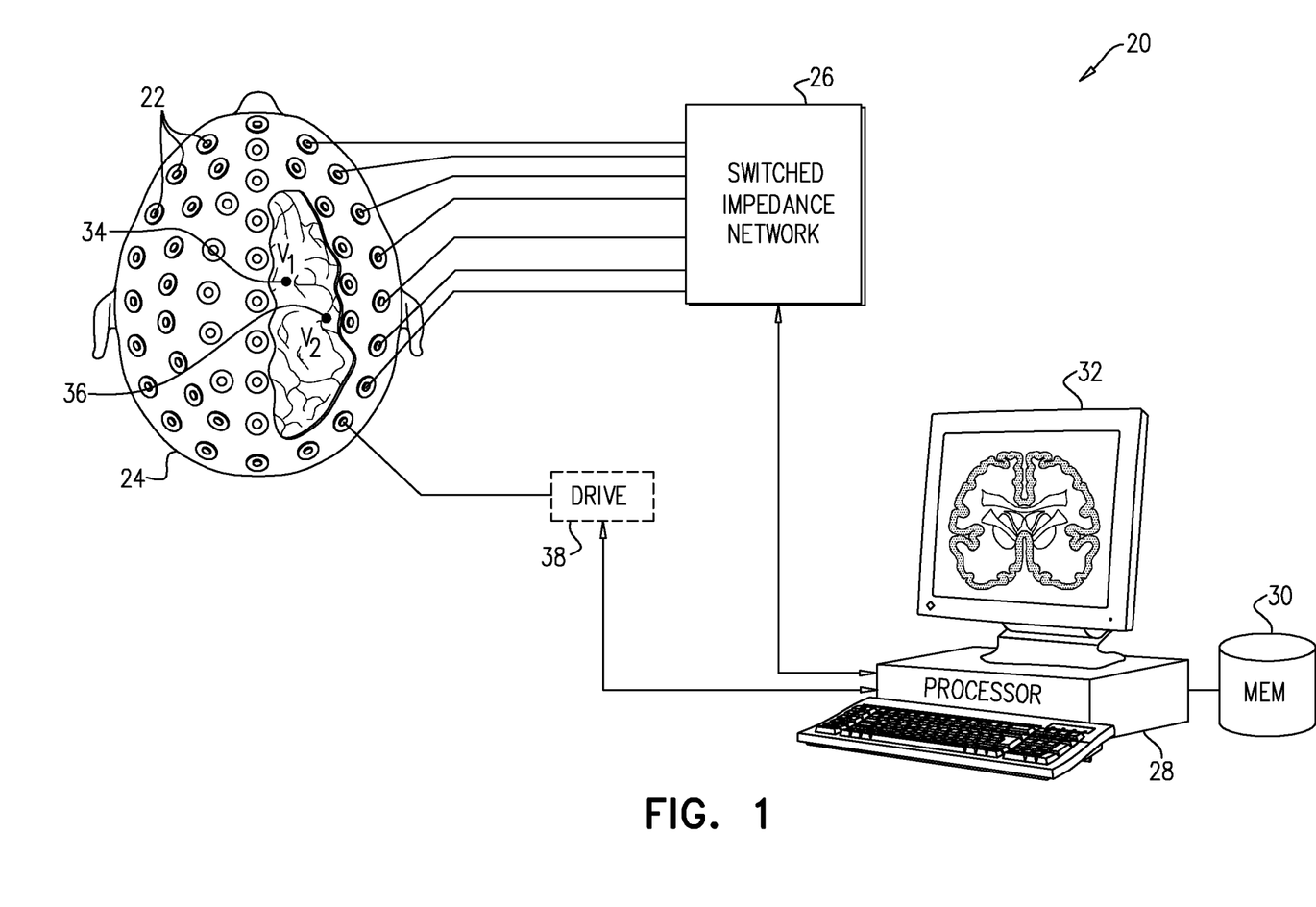
FIG. 1 is schematic pictorial illustration of a system for processing of electrical signals received from the body of a living subject, in accordance with an embodiment of the invention.

FIG. 1 is block diagram that schematically illustrates a system 20 for processing of signals received from a head 24 of a living subject, in accordance with an embodiment of the invention. System 20 comprises an array of electrodes 22, which are applied to the scalp at different, respective positions around head 24. Electrodes 22 are typically applied externally to the scalp, using an adhesive or gel, for example, to reduce their contact impedance. Alternatively, invasive electrodes, which penetrate the skin, may be used for better contact. Electrodes 22 may be arranged in a standard array, such as the well-known 10-20 electrode placement that is used in EEG measurements, or in any other suitable arrangement, with larger or smaller numbers of electrodes.

A switched impedance network 26 applies varying loads to the electrodes. A processor 28 receives and measures electrical signals from electrodes 22 via impedance network 26 as a function of the varying loads, and analyzes the measured signals so as to compute local electrical characteristics of one or more locations within the brain. For example, processor 28 may apply the measurements made by various electrodes 22 under different loads in order to distinguish a signal $V_1$ that is emitted from an internal location 34 deep inside the brain from a signal $V_2$ that is emitted from a surface location 36.

In some embodiments, processor 28 receives, via impedance network 26, signals that are generated spontaneously by the brain and other organs within head 24, such as EEG or EMG (electromyogram) signals, or even noise signals that arise within the head, due to power line radiation, for example. Alternatively or additionally, system 20 may comprise a field generator, which generates a time-varying electric field within head 24; and processor 28 may then measure the electrical signals output from the electrodes in response to this time-varying electric field. In the example shown in FIG. 1, the field generator comprises a driver 38, which applies a signal to one of electrodes 22 in order to generate the time-varying electric field. Alternatively, the field generator may be incorporated in an implantable device, as in the example shown in FIG. 4.

Processor 28 comprises a front end (not shown), which senses, amplifies, filters, and digitizes electrical signals received from electrodes 22 via network 26. On the basis of these signals and the known variation of the loads applied by network 26, processor 28 computes local electrical characteristics within the brain, for example voltages and/or impedances at locations 34 and 36. Typically, processor 28 uses the measurements made from different electrodes with different loads in calculating elements of the gain matrix G relating the currents generated at an array of locations in the brain to the signals measured by the various electrodes. Equivalently, processor 28 may calculate an impedance matrix Z between the locations in the brain and the electrodes or between different pairs of the electrodes. The theoretical basis and details of these computations are explained in the above-mentioned provisional application.

Typically, processor 28 comprises a general-purpose computer, which has suitable interfaces for communication with the other elements of system 20 and is programmed in software to carry out the functions that are described herein. This software may be stored, for example, on tangible, non-transitory computer-readable media, such as optical, magnetic, or electronic memory media. Alternatively, at least some of the functions of processor 28 may be carried out in hard-wired or programmable logic. Processor 28 typically saves the results of its computations in a memory 30 and presents the results in numerical and/or graphical form—for example as slices in an EIT image of the brain—on a display 32.

Figure 2:
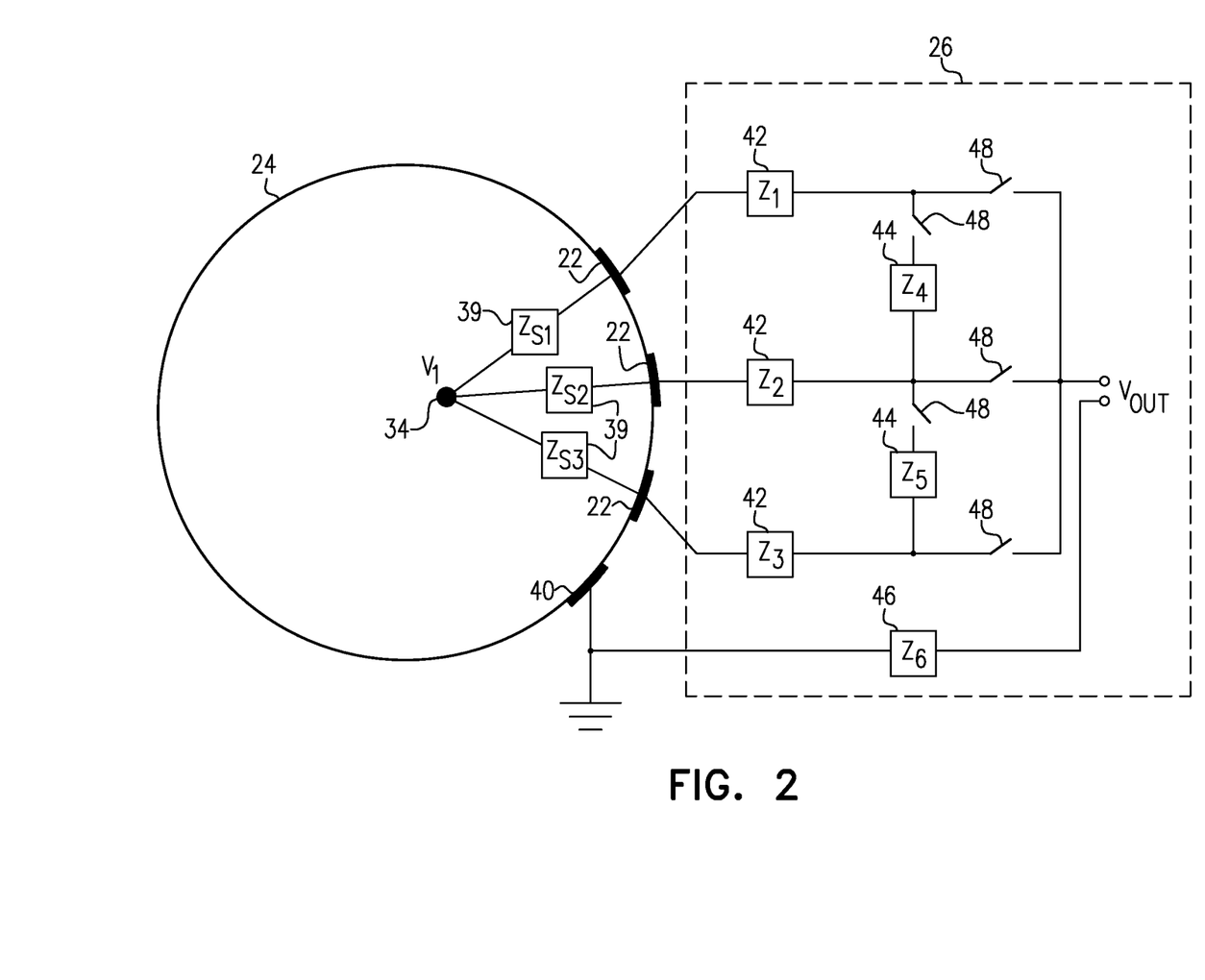
FIG. 2 is an electrical schematic diagram showing details of a switched impedance network connected to body-surface electrodes, in accordance with an embodiment of the invention.

FIG. 2 is an electrical schematic diagram showing details of switched impedance network 26 and its connections to electrodes 22, in accordance with an embodiment of the invention. Network 26 comprises multiple impedance components 42, 44, 46, which have respective values $Z_1$, $Z_2$, ..., and are interconnected by analog switches 48. Impedance components 42, 44, 46 may comprise resistors and/or capacitors, for example. Analog switches 48 may comprise, for example, DG417 precision CMOS analog switches, produced by Vishay Siliconix (Sunnyvale, California), or any other suitable device that is capable of switching at frequencies in the desired range, typically 1000 Hz or more, without generating substantial switching transients. Although FIG. 2 shows a certain specific configuration of the switches and impedance components, which permits both shunt and series impedances to be controlled, this configuration is shown only by way of example, and alternative network configurations will be apparent to those skilled in the art and are considered to be within the scope of the present invention.

Each location 34 within the brain is coupled to each of electrodes 22 through a corresponding source impedance 39, with values $Z_{S1}$, $Z_{S2}$, ..., due to the inherent impedance of the tissues within head 24 and the attachment impedance of the electrode to the scalp. A common electrode 40 serves as a ground. Impedance components 42 and 44 may advantageously comprise resistors, typically in the range of several hundred to several thousand ohms, comparable to or greater than impedances 39. Additionally or alternatively, when electrodes 22 are applied to the scalp without using gel or piercing the skin, impedances 39 typically comprise a substantial capacitive component. In this case, it can be advantageous to incorporate capacitors in impedance components 42 and/or 44, and to operate switches 48 at a high frequency in order to enhance the capacitive coupling between head 24 and the output $V_{OUT}$ of network 26 to processor 28.

Switches 48 may be operated at any suitable frequency, but generally speaking, the operation of network 26 falls into two broad regimes:

A static regime, in which the switches are opened at closed at rates substantially lower than the frequencies of the signals sensed by electrodes 22; and A dynamic regime, in which the switches are opened and closed at rates substantially higher than the signal frequencies (at least twice as high or even ten times higher), so that the signals are essentially constant over the switching period.

The static regime is most useful when a known high-frequency signal is applied to head 24, for example by driver 38 (FIG. 1). The signal can comprise a chirp signal (a frequency scan of unit amplitude), for example, or a linear combination of narrowband signals. This multi-frequency approach enables processor 28 to sample and characterize the spectral content of the impedance matrix at multiple frequencies. Switches 48 in impedance network 26 are held in constant positions during each pass of the excitatory signal and are modified between the passes.

In the dynamic regime, the low-frequency excitation signal, due to sources within or external to head 24, is modulated by switching the network of impedances at a sufficiently high frequency so that it can be assumed that within each switching period, the excitatory signal is close to constant up to a required precision. When the excitatory signal is itself a physiological signal, such as EEG waves, measurement of the impedance matrix can be completely passive: Excitation of electrodes 22 is provided by the physiological signal, and the impedance matrix is derived by switching of network 26 to alternately loading and releasing the loads on electrodes 22. Since only the difference of the measured voltage between different switch states, normalized by the current, is needed to extract the impedance matrix, processor 28 can derive the impedance matrix in this regime independently of the excitation signal and of the spatial distribution of the sources of the signal. Any noisy neural activity can be utilized to extract the impedance matrix in this manner. Alternatively or additionally, electrical noise, due to power line interference, for example, may be used in a similar fashion in this regime.

Methods of Operation

Figure 3:
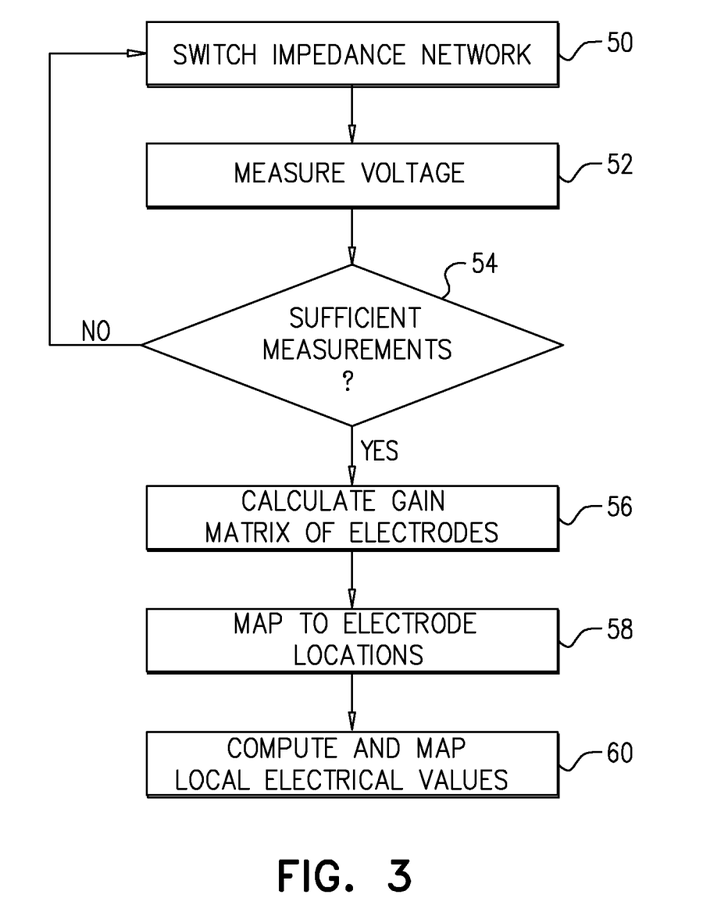
FIG. 3 is a flow chart that schematically illustrates a method for processing electrophysiological signals, in accordance with an embodiment of the invention.

FIG. 3 is a flow chart that schematically illustrates a method for processing electrophysiological signals, in accordance with an embodiment of the invention. The method is described here, for the sake of concreteness and clarity, with reference to the components of system 20 (FIGS. 1 and 2). Alternatively, however, this method may be applied, mutatis mutandis, in measuring local electrical characteristics within other regions and organs of the body, and using other sorts of switched impedance networks.

After electrodes 22 have been applied to head 24, processor 28 sets the positions of switches 48 in network 26, at a switching step 50, and then measures the output voltage $V_{OUT}$ from one or more of the electrodes, at a measurement step 52. This process of switching and measurement is repeated until processor 28 has collected sufficient data, at a measurement termination step 54. The number of cycles required depends on whether system 20 is operating in the static or dynamic regime (as defined above) and on the levels of precision and resolution that are required for the computation of the electrical characteristics of the brain.

Based on the measurements collected in the preceding steps, processor 28 computes the relevant gain matrix or, equivalently, the impedance matrix, at a matrix computation step 56. For example, each of the elements of the impedance matrix among electrodes 22 corresponds to the respective impedance value between a pair of electrodes 22. To compute these matrix elements, processor 28 may use values of the output voltage that were measured by network 26 with one of the electrodes in the pair grounded and the other connected to the output of the network through two different impedances. The difference between the two measured values of output voltage, relative to the difference between the impedances that were applied by network 26, is indicative of the internal impedance between the electrodes along a path through head 24. Each of the elements of the impedance matrix may be calculated successively in this manner. Alternatively, other switching and measurement configurations may be used in order to computed multiple impedance values concurrently.

To localize the impedance or gain values within head 24, processor 28 maps electrodes 22 to their respective three-dimensional (3D) coordinates on head 24, at a location mapping step 58. These 3D coordinates may be measured and recorded manually or using any suitable system of 3D mapping that is known in the art. Processor 28 then associates the impedance or gain values computed in step 56 with the coordinates assigned in step 58 in order to compute the local electrical characteristics of 3D locations within the head, at an electrical mapping step 60.

For example, for purposes of EIT, each element of the impedance matrix that was computed at step 56 can be associated with a corresponding line passing through head 24 in 3D space between the locations of the corresponding electrodes. Once all of the impedance matrix elements have been mapped in this fashion, processor 28 can apply a tomographic algorithm, as is known in the art, in order to derive the local impedance values at points within a plane passing through the brain (in a similar fashion to the computation of density in a CT image slice based on X-ray absorption along lines passing through the slice). Processor 28 can then render the local impedance values graphically in an EIT image, which is presented on display 32.

In another embodiment, processor 28 can use the elements of the gain matrix between a source of electrical signals in the brain and different electrodes 22 in finding the location of the source in three dimensions. Sources that are deeper in the brain, such as the source of signal $V_1$ at location 34 (FIG. 1) will have longer electrical paths to electrodes 22, with similar, high values of impedance over groups of neighboring electrodes. On the other hand, the source of signal $V_2$ at surface location 36 will have a low value of impedance to one or two of electrodes 22 and higher values to other electrodes. Processor 28 can thus estimate the coordinates of both locations.

Additionally or alternatively, processor 28 may use these estimated locations in filtering the electrophysiological signals. For example, the processor may filter out undesired signals, such as EMG artifacts, that are received from surface locations in order to enhance the signal/noise ratio of deep cortical signals. Alternatively, the processor may specifically extract signals from the brain surface or from other locations for further analysis.

Alternative Embodiments and Applications

Figure 4:
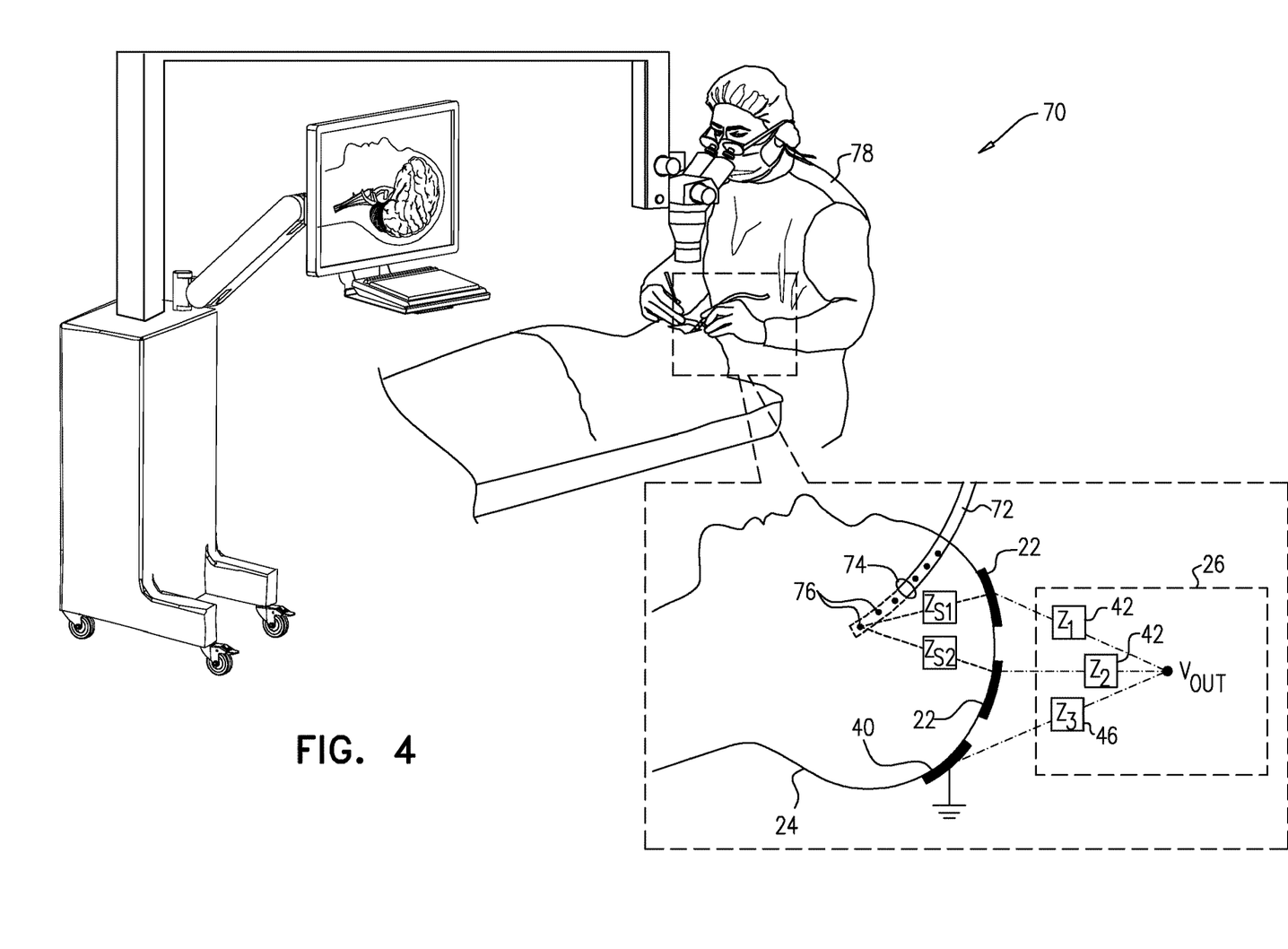
FIG. 4 is a schematic pictorial illustration of a system used in insertion of a subdural strip into the skull of a patient, in accordance with an embodiment of the invention.

FIG. 4 is a schematic pictorial illustration of a system 70 used in insertion of a subdural strip 72 into the skull of a patient, in accordance with an embodiment of the invention. Processor 28 and details of network 26 are omitted from this figure for the sake of simplicity. A surgeon 78 inserts strip 72 through a burr hole 74 in the skull. Strip 72 comprises an array of electrodes 76, which are able to sense cortical electrical activity with greater precision than is possible using scalp electrodes 22.

Strip 72 tends to be flexible, and surgeon 78 is generally unable to see the part of the strip that is inside head 24. Furthermore, the strip may shift after insertion. Imaging techniques, such as X-ray imaging or MRI, may be used to visualize the location of the strip and verify proper placement, but such imaging complicates the process and exposes the patient to undesirable radiation.

The embodiment of FIG. 4 addresses this problem using the signal processing techniques described above. For this purpose, driver 38 (FIG. 1) applies a signal to one of electrodes 76, which causes the electrode to generate a time-varying electric field. The frequency and amplitude of the signal are typically chosen so that the electric field does not stimulate the brain tissue. Processor 28 receives electrical signals from electrodes 22 while switching the impedances applied by network 26 to the electrodes. Based on the measured signals, processor 28 computes the values of the gain matrix elements between electrodes 76 and 22, and is thus able to derive the coordinates of strip 76 within head 24.

As another example, the techniques described above may be used in detection of pulmonary edema, which often occurs due to congestive heart failure. In pulmonary edema, fluid accumulates in the air spaces of the lungs and thus influences the conductivity of the lungs. A switched impedance network can be used to measure the influence of these conductivity changes on the propagation of ECG signals from the heart through the body to electrodes on the body surface. The measured impedance can be used in constructing EIT images of the lungs, as well as detecting locations of fluid build-up.

In another embodiment, a switched impedance network can be used in electromyography (EMG), for evaluating and recording the electrical activity produced by skeletal muscles. Body-surface EMG measurements are sensitive mainly to muscles that are close to the skin. Intramuscular EMG measurement is more exact than body-surface EMG, but it is typically performed as an invasive procedure, resulting in pain and possible infection. In order to detect intramuscular EMG non-invasively, a switched impedance network can be used to distinguish deep EMG sources from sources near the body surface, in a manner similar to the EEG filtering technique described above.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system for finding a local electrical characteristic within a body of a living subject, the system comprising:
    an array of electrodes, which are configured to be coupled to a body surface of the living subject at different, respective positions in proximity to a region of interest within the body;
    a switched impedance network, which is configured to apply varying impedances between the electrodes and an output of the switched impedance network; and
    a processor, which is coupled to the output to receive and measure multiple electrical signals from the electrodes at different, respective values of the varying impedances, and to analyze the measured electrical signals so as to compute the local electrical characteristic of one or more locations in an internal layer of the body within the region of interest.

2. The system according to claim 1, wherein the switched impedance network comprises a plurality of impedance components interconnected by analog switches.

3. The system according to claim 2, wherein the impedance components are selected from a group of components consisting of resistors and capacitors.

4. The system according to claim 1, wherein the electrodes are configured to sense an electrical activity in the body having a maximal frequency, and the processor is configured to receive and measure the electrical signals due to the sensed electrical activity while varying the impedances applied by the switched impedance network at a rate greater than twice the maximal frequency.

5. The system according to claim 4, wherein the rate of varying the impedances applied by the switched impedance network is at least ten times the maximal frequency.

6. The system according to 4, wherein the region of interest is a head of the subject, and wherein the electrodes are configured to sense an electroencephalogram (EEG) of the subject.

7. The system according to claim 1, and comprising a field generator, which is configured to generate a time-varying electric field within the region of interest, and wherein the processor is configured to measure the electrical signals output from the electrodes in response to the time-varying electric field.

8. The system according to claim 7, wherein the field generator comprises a driver, which is coupled to drive an electrode in the array of electrodes coupled to the body surface of the subject to generate the time-varying electric field.

9. The system according to claim 7, wherein the field generator is incorporated in an implantable device.

10. The system according to claim 9, wherein the processor is configured to find a location of the implantable device within the body by analyzing the measured signals.

11. The system according to claim 1, wherein the processor is configured to analyze the measured electrical signals so as to identify a location of a source of a signal within the region of interest.

12. The system according to claim 1, wherein the processor is configured to analyze the measured electrical signals so as to estimate local electrical impedances of the one or more locations within the region of interest.

13. The system according to claim 12, wherein the processor is configured to estimate the local electrical impedances by finding a matrix of the impedances between the electrodes in the array, and associating the matrix of the impedances with the respective positions of the electrodes in order to find the local electrical impedances of the one or more locations.

14. The system according to claim 13, wherein the processor is configured to generate and output an electrical impedance tomogram incorporating the local electrical impedances.

15. A method for finding a local electrical characteristic within a body of a living subject, the method comprising:
    coupling an array of electrodes to a body surface of the living subject at different, respective positions in proximity to a region of interest within the body;
    applying, using a switched impedance network connected to the electrodes, varying impedances between the electrodes and an output of the switched impedance network;
    receiving, via the output, and measuring multiple electrical signals from the electrodes at different, respective values of the varying impedances; and
    analyzing the measured electrical signals so as to compute the local electrical characteristic of one or more locations in an internal layer of the body within the region of interest.

16. The method according to claim 15, wherein the switched impedance network comprises a plurality of impedance components interconnected by analog switches.

17. The method according to claim 16, wherein the impedance components are selected from a group of components consisting of resistors and capacitors.

18. The method according to claim 15, wherein the electrodes are configured to sense an electrical activity in the body having a maximal frequency, and wherein receiving and measuring the multiple electrical signals comprises receiving the multiple electrical signals due to the sensed electrical activity while varying the impedances applied by the switched impedance network at a rate greater than twice the maximal frequency.

19. The method according to claim 18, wherein the rate of varying the impedances applied by the switched impedance network is at least ten times the maximal frequency.

20. The method according to 18, wherein the region of interest is a head of the subject, and wherein the electrodes are configured to sense an electroencephalogram (EEG) of the subject.

21. The method according to claim 15, and comprising generating a time-varying electric field within the region of interest, and wherein receiving and measuring the multiple electrical signals comprises measuring the electrical signals output from the electrodes in response to the time-varying electric field.

22. The method according to claim 21, wherein generating the time-varying electric field comprises driving an electrode in the array of electrodes coupled to the body surface of the subject to generate the time-varying electric field.

23. The method according to claim 21, wherein the time-varying electric field is generated by an implantable device.

24. The method according to claim 23, wherein analyzing the measured electrical signals comprises finding a location of the implantable device within the body by analyzing the measured signals.

25. The method according to claim 15, wherein analyzing the measured electrical signals comprises identifying a location of a source of a signal within the region of interest.

26. The method according to claim 15, wherein analyzing the measured electrical signals comprises estimating local electrical impedances of the one or more locations within the region of interest.

27. The method according to claim 26, wherein estimating the local electrical impedances comprises finding a matrix of the impedances between the electrodes in the array, and associating the matrix of the impedances with the respective positions of the electrodes in order to find the local electrical impedances of the one or more locations.

28. The method according to claim 27, and comprising generating and outputting an electrical impedance tomogram incorporating the local electrical impedances.

* * * * *